(12) United States Patent
Bradshaw et al.

(10) Patent No.: US 10,076,487 B2
(45) Date of Patent: *Sep. 18, 2018

(54) COMFORTABLE, LONG-WEARING, TRANSFER-RESISTANT COLORED COSMETIC COMPOSITIONS

(75) Inventors: Kimberly Bradshaw, Monmouth Junction, NJ (US); Hy Si Bui, Piscataway, NJ (US)

(73) Assignee: L'OREAL, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 12/982,061

(22) Filed: Dec. 30, 2010

(65) Prior Publication Data
US 2012/0171139 A1 Jul. 5, 2012

(51) Int. Cl.
| | |
|---|---|
| A61K 8/92 | (2006.01) |
| A61Q 1/04 | (2006.01) |
| A61Q 5/06 | (2006.01) |
| A61Q 1/02 | (2006.01) |
| A61K 8/891 | (2006.01) |
| A61K 8/31 | (2006.01) |
| A61Q 1/06 | (2006.01) |
| A61K 8/898 | (2006.01) |

(52) U.S. Cl.
CPC .......... *A61K 8/891* (2013.01); *A61K 8/31* (2013.01); *A61K 8/898* (2013.01); *A61Q 1/06* (2013.01); *A61K 2800/31* (2013.01); *A61K 2800/43* (2013.01); *A61K 2800/5922* (2013.01)

(58) Field of Classification Search
None
See application file for complete search history.

(56) References Cited

U.S. PATENT DOCUMENTS

| | | | |
|---|---|---|---|
| 5,874,069 A | 2/1999 | Mendolia et al. | |
| 5,919,441 A | 7/1999 | Mendolia et al. | |
| 5,981,680 A | 11/1999 | Petroff et al. | |
| 6,051,216 A | 4/2000 | Barr et al. | |
| 6,964,773 B1 | 11/2005 | Morrison | |
| 7,842,285 B2 | 11/2010 | Lu et al. | |
| 7,879,316 B2 | 2/2011 | Ferrari et al. | |
| 2007/0093619 A1* | 4/2007 | Bui et al. ............... | 525/477 |
| 2007/0149703 A1 | 6/2007 | Caprasse et al. | |
| 2008/0166309 A1* | 7/2008 | McDermott et al. ....... | 424/64 |
| 2008/0171006 A1 | 7/2008 | Bui et al. | |
| 2008/0305061 A1* | 12/2008 | Bui et al. ............. | 424/63 |

FOREIGN PATENT DOCUMENTS

| | | |
|---|---|---|
| EP | 1 854 450 A2 | 11/2007 |
| WO | WO 2005/100444 | 10/2005 |
| WO | WO2005/100444 | * 10/2005 |

OTHER PUBLICATIONS

Dow Corning 670 Fluid, http://www.dowcorning.com/applications/search/products/details.aspx?prod=0402387&type=PROD, accessed Jul. 19, 2012.*
Dow Corning, "Dow Corning® SW-8005 C30 Resin Wax", http://www.dowcorning.com/DataFiles/090276fe8018fe50.pdf, accessed Mar. 3, 2015.*
U.S. Appl. No. 12/981,867, filed Dec. 30, 2010, Bui et al.
U.S. Appl. No. 12/982,108, filed Dec. 30, 2010, Bui et al.
U.S. Appl. No. 12/982,061, filed Dec. 30, 2010, Bradshaw et al.
U.S. Appl. No. 12/981,839, filed Dec. 30, 2010, Bradshaw et al.
U.S. Appl. No. 12/981,882, filed Dec. 30, 2010, Bradshaw et al.
Amendment filed in U.S. Appl. No. 12/981,839 dated Jun. 25, 2013.
Office Action dated Apr. 22, 2014 in European Patent Application No. 11807934.2.
International Preliminary Report on Patentability dated Mar. 13, 2014, in EP Patent Application No. PCT/EP2011/074016.
International Search Report and Written Opinion dated Feb. 21, 2014 in PCT/EP2011/074016.
Adriana Urrutia, et al., "Silicone Polyamide: An Innovative Structurant for Personal Care Applications" Dow Corning, XP002476529, 2003, 15 pages http://www.dowcorning.com/content/publishedlit/27-1086-01.pdf.
Office Action as received in the corresponding European Patent Application No. 11 807 934.2-1468 dated Jan. 27, 2017.

* cited by examiner

*Primary Examiner* — Melissa L Fisher
(74) *Attorney, Agent, or Firm* — Oblon, McClelland, Maier & Neustadt, L.L.P.

(57) ABSTRACT

The present invention is directed to an anhydrous composition which is long wearing and transfer resistant, while at the same time providing superior comfort, feel and cushioning, the composition containing: (a) at least one polypropylsilsesquioxane wax substituted with alkyl units having at least 30 carbons; (b) at least one siloxysilicate resin; (c) at least one polyorganosiloxane-containing polymer; (d) at least one volatile solvent; (e) optionally, at least one non-volatile solvent; and (f) at least one colorant.

15 Claims, No Drawings

COMFORTABLE, LONG-WEARING, TRANSFER-RESISTANT COLORED COSMETIC COMPOSITIONS

BACKGROUND OF THE INVENTION

Cosmetic compositions used to make up a user's skin must be able to impart color with little to no transfer. They must also provide good wear properties. The transfer resistance and wear of cosmetic compositions are usually obtained through the use of film forming resins such as silicone film forming resins. While the use of silicone film forming resins in colored cosmetics is popular, one drawback associated with their use is that they tend to be brittle and flake off. This phenomenon results in the need to use a plasticizer, in combination with the resin, in order to render the resultant film more flexible and, hence, less susceptible to flake off and poor transfer resistance. Moreover, the resultant films formed by the resins are uncomfortable on human skin.

Therefore, it is an object of the present invention to provide a method and composition for making up skin in a manner which delivers a combination of long wear, transfer resistance, superior comfort and feel.

BRIEF SUMMARY OF THE INVENTION

According to one embodiment of the present invention, there is provided an anhydrous composition which is long wearing and transfer resistant, while at the same time providing superior comfort, feel and cushioning, the composition containing:

(a) at least one polypropylsilsesquioxane wax substituted with alkyl units having at least 30 carbons;
(b) at least one siloxysilicate resin;
(c) at least one polyorganosiloxane-containing polymer;
(d) at least one volatile solvent;
(e) optionally, at least one non-volatile solvent; and
(f) at least one colorant.

According to another aspect of the present invention, there is provided a method of making up skin involving applying onto the skin the above-disclosed composition.

It has been surprisingly discovered that the above-described cosmetic composition provides long wear, superior transfer resistance and comfort when applied onto a keratinous substrate.

DETAILED DESCRIPTION OF THE INVENTION

As used herein, the expression "at least one" means one or more and thus includes individual components as well as mixtures/combinations.

Other than in the operating examples, or where otherwise indicated, all numbers expressing quantities of ingredients and/or reaction conditions are to be understood as being modified in all instances by the term "about," meaning within 10% to 15% of the indicated number.

"Film former" or "film forming agent" as used herein means a polymer or resin that leaves a film on the substrate to which it is applied, for example, after a solvent accompanying the film former has evaporated, absorbed into and/or dissipated on the substrate.

"Transfer resistance" as used herein refers to the quality exhibited by compositions that are not readily removed by contact with another material, such as, for example, a glass, an item of clothing or the skin, for example, when eating or drinking. Transfer resistance may be evaluated by any method known in the art for evaluating such. For example, transfer resistance of a composition may be evaluated by a "kiss" test. The "kiss" test may involve application of the composition to human keratin material such as hair, skin or lips followed by rubbing a material, for example, a sheet of paper, against the hair, skin or lips after expiration of a certain amount of time following application, such as 2 minutes after application. Similarly, transfer resistance of a composition may be evaluated by the amount of product transferred from a wearer to any other substrate, such as transfer from the hair, skin or lips of an individual to a collar when putting on clothing after the expiration of a certain amount of time following application of the composition to the hair, skin or lips. The amount of composition transferred to the substrate (e.g., collar, or paper) may then be evaluated and compared. For example, a composition may be transfer resistant if a majority of the product is left on the wearer's hair, skin or lips. Further, the amount transferred may be compared with that transferred by other compositions, such as commercially available compositions. In a preferred embodiment of the present invention, little or no composition is transferred to the substrate from the hair, skin or lips.

"Long wear" compositions as used herein, refers to compositions where color remains the same or substantially the same as at the time of application, as viewed by the naked eye, after an extended period of time. Long wear properties may be evaluated by any method known in the art for evaluating such properties. For example, long wear may be evaluated by a test involving the application of a composition to human hair, skin or lips and evaluating the color of the composition after an extended period of time. For example, the color of a composition may be evaluated immediately following application to hair, skin or lips and these characteristics may then be re-evaluated and compared after a certain amount of time. Further, these characteristics may be evaluated with respect to other compositions, such as commercially available compositions.

"Substituted" as used herein, means comprising at least one substituent. Non-limiting examples of substituents include atoms, such as oxygen atoms and nitrogen atoms, as well as functional groups, such as amine groups, ether groups, alkoxy groups, acyloxyalky groups, oxyalkylene groups, polyoxyalkylene groups, carboxylic acid groups, amine groups, acylamino groups, amide groups, halogen containing groups, ester groups, thiol groups, sulphonate groups, thiosulphate groups, siloxane groups, and polysiloxane groups. The substituent(s) may be further substituted.

The compositions and methods of the present invention can comprise, consist of, or consist essentially of the essential elements and limitations of the invention described herein, as well as any additional or optional ingredients, components, or limitations described herein or otherwise useful.

The cosmetic compositions of the present invention comprise at least one polypropylsilsesquioxane wax substituted with alkyl units having at least 30 carbons.

Polypropylsilsesquioxane waxes, in general, have been disclosed in patent publication WO2005/100444, published on Oct. 27, 2005, the entire content of which is hereby incorporated by reference.

It should be noted, however, that not all polypropylsilsesquioxane waxes yield stable colored cosmetic emulsion products. More particularly, it has been found that only those polypropylsilsesquioxane waxes substituted with alkyl units having at least 30 carbons are stable.

The polypropylsilsesquioxane wax comprises at least mole % of siloxy units having the formula (R2R'SiO1/2)x (C3H7SiO3/2)y, where x and y have a value of 0.05 to 0.95, R is an alkyl group having from 1 to 8 carbon atoms, and R' is a monovalent hydrocarbon having 30 to 40 carbon atoms and greater. As used herein, x and y represent the mole fraction of (R2R'SiO1/2) and (C3H7SiO3/2) siloxy units relative to each other present in the polypropylsilsesquioxane wax. Thus, the mole fraction of (R2R'SiO1/2) and (C3H7SiO3/2) siloxy units each can independently vary from 0.05 to 0.95. Preferably R is a methyl, and R' is an alkyl having at least 30 carbons, available from Dow Corning.

Typically, the value of x is 0.05 to 0.95, or alternatively, 0.2 to 0.8, the value of y is 0.05 to 0.95, alternatively 0.2 to 0.8. However, the combination of (R2R'SiO1/2) and (C3H7SiO3/2) siloxy units present must total at least 40 mole %, alternatively 60 mole %, or alternatively mole % of all siloxy units present in the polypropylsilsesquioxane wax.

The number average molecular weight of the polypropylsilsesquioxane wax substituted with alkyl units having at least 30 carbons typically ranges from about 750 to about 10,000, such as from about 1,000 to about 5,000.

A particularly preferred polypropylsilsesquioxane wax for use in the present invention is a C30-45 ALKYLDIMETHYLSILYL POLYPROPYLSILSESQUIOXANE commercially available from DOW CORNING under the tradename SW-8005 C30 RESIN WAX.

The polypropylsilsesquioxane wax substituted with alkyl units having at least 30 carbons is generally present in the cosmetic composition of the present invention in an amount ranging from about 0.1% to about 10% by weight; such as from about 0.5% to about 5% by weight; such as from about 0.75% to about 2.5% by weight, all weights being based on the weight of the composition as a whole.

The cosmetic compositions of the present invention further comprise at least one siloxysilicate. One non-limiting example of a siloxysilicate in accordance with the present invention is trimethylsiloxysilicate, which may be represented by the following formula:

wherein x and y may, for example, range from 50 to 80. Such siloxysilicates are commercially available from General Electric and Dow Corning under the tradename Resin MQ®.

The at least one siloxysilicate is generally present in the cosmetic composition of the present invention in an amount ranging from about 5% to about 30% by weight; such as from about 10% to about 25% by weight; such as from about 15% to about 20% by weight, all weights being based on the weight of the composition as a whole.

The cosmetic compositions of the present invention also comprise at least one polyorganosiloxane-containing polymer. The polyorganosiloxane-containing polymer useful herein is a polymer (homopolymer or copolymer) having at least one moiety which contains: at least one polyorganosiloxane group consisting of 1 to about 1000 organosiloxane units in the chain of the moiety or in the form of a graft, and at least two groups capable of establishing hydrogen interactions.

The polyorganosiloxane-containing polymers may comprise at least one moiety corresponding to formula (I):

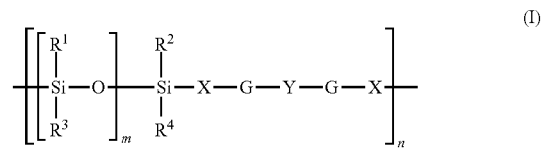

in which:
1) $R^1$, $R^2$, $R^3$ and $R^4$, which may be identical or different, represent a group chosen from:
   (a) linear, branched or cyclic, saturated or unsaturated, $C_1$ to $C_{40}$ hydrocarbon-based groups, possibly containing in their chain one or more oxygen, sulphur and/or nitrogen atoms, and possibly being partially or totally substituted with fluorine atoms,
   (b) $C_6$ to $C_{10}$ aryl groups, optionally substituted with one or more $C_1$ to $C_4$ alkyl groups,
   (c) polyorganosiloxane chains possibly containing one or more oxygen, sulphur and/or nitrogen atoms;
2) X, which may be identical or different, represents a linear or branched $C_1$ to $C_{30}$ alkylenediyl group, possibly containing in its chain one or more oxygen and/or nitrogen atoms;
3) Y is a saturated or unsaturated, $C_1$ to $C_{50}$ linear or branched divalent alkylene, arylene, cycloalkylene, alkylarylene or arylalkylene group, optionally comprising one or more oxygen, sulphur and/or nitrogen atoms, and/or optionally substituted with one of the following atoms or groups of atoms: fluorine, hydroxyl, $C_3$ to $C_8$ cycloalkyl, $C_1$ to $C_{40}$ alkyl, $C_5$ to $C_{10}$ aryl, phenyl optionally substituted with one to three $C_1$ to $C_3$ alkyl, $C_1$ to $C_3$ hydroxyalkyl, and $C_1$ to $C_6$ aminoalkyl groups;
4) G, which may be identical or different, represents a group chosen from ester, amide, sulphonamide, carbamate, thiocarbamate, urea, thiourea groups, and combinations thereof;
5) m is an integer ranging from 1 to 1,000, preferably from 1 to 700 and more preferably from 6 to 200; and
6) n is an integer ranging from 2 to 500 and preferably from 2 to 200.

The polyorganosiloxane-containing polymers may also comprise at least one moiety corresponding to formula (II):

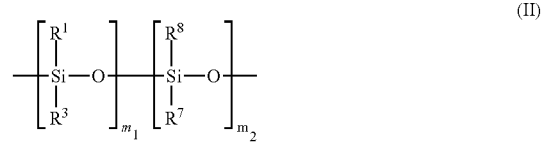

in which
$R^1$ and $R^3$, which may be identical or different, are as defined above for formula (I),
$R^7$ represents a group as defined above for $R^1$ and $R^3$, or represents a group of formula —X-G-$R^9$ in which X and G are as defined above for formula (I) and $R^9$ represents a hydrogen atom or a linear, branched or cyclic, saturated or unsaturated, $C_1$ to $C_{50}$ hydrocarbon-based group optionally comprising in its chain one or more atoms chosen from O, S and N, optionally substituted with one or more fluorine atoms and/or one or more hydroxyl groups, or a phenyl group optionally substituted with one or more $C_1$ to $C_4$ alkyl groups, $R^8$ represents a group of formula —X-G-$R^9$ in which X, G and $R^9$ are as defined above, $m_1$ is an integer ranging from 1 to 998, and $m_2$ is an integer ranging from 2 to 500.

According to another embodiment, it is also possible to use a copolymer comprising several different moieties of formula (I), and/or several different moieties of formula (II), that is to say a polymer in which at least one of the groups $R^1$, $R^2$, $R^3$, $R^4$, X, G, Y, m and n is different in one of the moieties.

It is also possible to use a copolymer comprising at least one moiety of formula (I) and at least one moiety of formula (II), the moieties of formula (I) and the moieties of formula (II) possibly being identical to, or different from, each other. These copolymers may be block copolymers or grafted copolymers.

Additional polyorganosiloxane-containing polymers which may be used in the composition of the invention include those described in documents U.S. Pat. No. 5,874,069, U.S. Pat. No. 5,919,441, U.S. Pat. No. 6,051,216, and U.S. Pat. No. 5,981,680, the entire contents of which are hereby incorporated by reference.

A preferred polyorganosiloxane-containing polymer for use in the present invention will have at least one moiety chosen from formula (III):

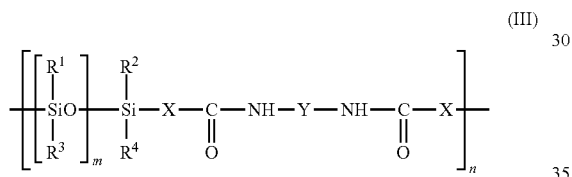

(III)

and formula (IV)

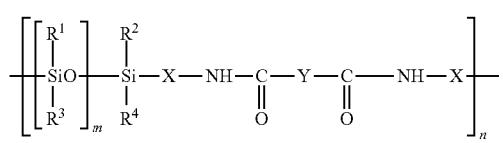

(IV)

in which:

(a) $R^1$, $R^2$, $R^3$ and $R^4$ are the same or different and may be selected from the group consisting of methyl, ethyl, propyl, isopropyl, a siloxane chain, and phenyl;

(b) X is a linear or branched chain alkylene having 1-30 carbons;

(c) Y is selected from the group consisting of linear or branched chain alkylenes having 1-40 carbons;

(d) m is a number between 1 and 700;

(e) n is a number between 1 and 500.

Particularly preferred polyorganosiloxane-containing polymers useful herein are commercially available from Dow Corning as DC 8178 and DC 8179, which are known under the INCI denomination of Nylon-611/Dimethicone Copolymer.

The at least one polyorganosiloxane-containing polymer is generally present in the cosmetic composition of the present invention in an amount ranging from about 5% to about 25% by weight; such as from about 7.5% to about 20% by weight; such as from about 10% to about 15% by weight, all weights being based on the weight of the composition as a whole.

The composition of the invention also contains at least one volatile solvent.

The expression "volatile solvent" means any non-aqueous medium capable of evaporating on contact with the skin or the lips in less than one hour at room temperature and atmospheric pressure.

Examples of suitable volatile solvents include volatile hydrocarbon-based oils such as, for example, volatile hydrocarbon oils having from 8 to 16 carbon atoms and their mixtures and in particular branched $C_8$ to $C_{16}$ alkanes such as $C_8$ to $C_{16}$ isoalkanes (also known as isoparaffins), isododecane, isodecane, isohexadecane, and for example, the oils sold under the trade names of Isopar or Permethyl, the $C_8$ to $C_{16}$ branched esters such as isohexyl or isodecyl neopentanoate, alcohols, and their mixtures. Preferably, the volatile hydrocarbon-based oils have a flash point of at least 40° C.

Examples of volatile hydrocarbon-based oils include, but are not limited to those given in Table 1 below.

TABLE 1

| Compound | Flash Point (° C.) |
| --- | --- |
| Isododecane | 43 |
| Isohexadecane | 102 |
| Isodecyl neopentanoate | 118 |
| Propylene glycol n-butyl ether | 60 |
| Ethyl 3-ethoxypropionate | 58 |
| Propylene glycol methylether acetate | 46 |
| Isopar L (isoparaffin $C_{11}$-$C_{13}$) | 62 |
| Isopar H (isoparaffin $C_{11}$-$C_{12}$) | 56 |

The volatile solvent may also be chosen from volatile silicone oils, which may be linear or cyclic, having a viscosity, at room temperature, of less than or equal to 6 cSt, and having, from 2 to 7 silicon atoms, optionally substituted with alkyl or alkoxy groups of 1 to 10 carbon atoms.

Examples of suitable volatile silicone oils include, but are not limited to, those listed in Table 2 below.

TABLE 2

| Compound | Flash Point (° C.) | Viscosity (cSt) |
| --- | --- | --- |
| Octyltrimethicone | 93 | 1.2 |
| Hexyltrimethicone | 79 | 1.2 |
| Decamethylcyclopentasiloxane (cyclopentasiloxane or D5) | 72 | 4.2 |
| Octamethylcyclotetrasiloxane (cyclotetradimethylsiloxane or D4) | 55 | 2.5 |
| Dodecamethylcyclohexasiloxane (D6) | 93 | 7 |
| Decamethyltetrasiloxane (L4) | 63 | 1.7 |
| KF-96 A from Shin Etsu | 94 | 6 |
| PDMS (polydimethylsiloxane) DC 200 (1.5 cSt) from Dow Corning | 56 | 1.5 |
| PDMS DC 200 (2 cSt) from Dow Corning | 87 | 2 |
| PDMS DC 200 (5 cSt) from Dow Corning | 134 | 5 |
| PDMS DC 200 (3 St) from Dow Corning | 102 | 3 |

The at least one volatile solvent is generally present in the cosmetic composition of the present invention in an amount ranging from about 25% to about 70% by weight; such as from about 30% to about 50% by weight; such as from about 35% to about 40% by weight, all weights being based on the weight of the composition as a whole.

The compositions of the present invention may further comprise at least one non-volatile solvent. Examples of suitable non-volatile solvents include, but are not limited to, polar oils such as:

hydrocarbon-based plant oils with a high triglyceride content consisting of fatty acid esters of glycerol, the fatty acids of which may have varied chain lengths, these chains possibly being linear or branched, and saturated or unsaturated; these oils are especially wheat germ oil, corn oil, sunflower oil, karite butter, castor oil, sweet almond oil, macadamia oil, apricot oil, soybean oil, rapeseed oil, cottonseed oil, alfalfa oil, poppy oil, pumpkin oil, sesame seed oil, marrow oil, avocado oil, hazelnut oil, grape seed oil, blackcurrant seed oil, evening primrose oil, millet oil, barley oil, quinoa oil, olive oil, rye oil, safflower oil, candlenut oil, passion flower oil or musk rose oil; or caprylic/capric acid triglycerides, for instance those sold by the company Stearineries Dubois or those sold under the names Miglyol 810, 812 and 818 by the company Dynamit Nobel;

synthetic oils or esters of formula R5COOR6 in which R5 represents a linear or branched higher fatty acid residue containing from 1 to 40 carbon atoms, including from 7 to 19 carbon atoms, and $R_6$ represents a branched hydrocarbon-based chain containing from 1 to 40 carbon atoms, including from 3 to 20 carbon atoms, with $R_6+R_7 \square 10$, such as, for example, Purcellin oil (cetostearyl octanoate), isononyl isononanoate, $C_{12}$ to $C_{1-5}$ alkyl benzoate, isopropyl myristate, 2-ethylhexyl palmitate, and octanoates, decanoates or ricinoleates of alcohols or of polyalcohols; hydroxylated esters, for instance isostearyl lactate or diisostearyl malate; and pentaerythritol esters;

synthetic ethers containing from 10 to 40 carbon atoms; $C_8$ to $C_{26}$ fatty alcohols, for instance oleyl alcohol; and mixtures thereof.

Further, examples of non-volatile oils that may be used in the present invention include, but are not limited to, non-polar oils such as silicone oils, branched and unbranched hydrocarbons and hydrocarbon waxes including polyolefins, in particular Vaseline (petrolatum), paraffin oil, squalane, squalene, hydrogenated polyisobutene, hydrogenated polydecene, polybutene, mineral oil, pentahydrosqualene, and mixtures thereof.

According to one embodiment of the present invention, the non-volatile solvent is a non-volatile silicone, pentaphenyldimethicone, also known as trimethyl pentaphenyl trisiloxane, and commercially available from Dow Corning under the tradename DC555®.

The at least one non-volatile solvent may be present in the cosmetic composition of the present invention in an amount ranging from about 1% to about 40% by weight; such as from about 5% to about 30% by weight; such as from about 10% to about 20% by weight, all weights being based on the weight of the composition as a whole.

The cosmetic compositions of the present invention also contain at least one cosmetically acceptable colorant such as a pigment or dyestuff. Examples of suitable pigments include, but are not limited to, inorganic pigments, organic pigments, lakes, pearlescent pigments, irridescent or optically variable pigments, and mixtures thereof. A pigment should be understood to mean inorganic or organic, white or colored particles. Said pigments may optionally be surface-treated within the scope of the present invention but are not limited to treatments such as silicones, perfluorinated compounds, lecithin, and amino acids.

Representative examples of inorganic pigments useful in the present invention include those selected from the group consisting of rutile or anatase titanium dioxide, coded in the Color Index under the reference CI 77,891; black, yellow, red and brown iron oxides, coded under references CI 77,499, 77, 492 and, 77,491; manganese violet (CI 77,742); ultramarine blue (CI 77,007); chromium oxide (CI 77,288); chromium hydrate (CI 77,289); and ferric blue (CI 77,510) and mixtures thereof.

Representative examples of organic pigments and lakes useful in the present invention include, but are not limited to, D&C Red No. 19 (CI 45,170), D&C Red No. 9 (CI 15,585), D&C Red No. 21 (CI 45,380), D&C Orange No. 4 (CI 15,510), D&C Orange No. 5 (CI 45,370), D&C Red No. 27 CI 45,410), D&C Red No. 13 (CI 15,630), D&C Red No. 7 CI 15,850), D&C Red No. 6 (CI 15,850), D&C Yellow No. 5 CI 19,140), D&C Red No. 36 (CI 12,085), D&C Orange No. 10 CI 45,425), D&C Yellow No. 6 (CI 15,985), D&C Red No. 30 CI 73,360), D&C Red No. 3 (CI 45,430) and the dye or lakes based on cochineal carmine (CI 75,570) and mixtures thereof.

Representative examples of pearlescent pigments useful in the present invention include those selected from the group consisting of the white pearlescent pigments such as mica coated with titanium oxide, mica coated with titanium dioxide, bismuth oxychloride, titanium oxychloride, colored pearlescent pigments such as titanium mica with iron oxides, titanium mica with ferric blue, chromium oxide and the like, titanium mica with an organic pigment of the above-mentioned type as well as those based on bismuth oxychloride and mixtures thereof.

The precise amount and type of colorant employed in the compositions of the present invention will depend on the color, intensity and use of the cosmetic composition and, as a result, will be determined by those skilled in the art of cosmetic formulation. However, one preferred amount of colorant for use in the present invention is from about 0.5% to about 7.5%, based on the weight of the composition.

Additives/Auxiliary Agents

The compositions of the present invention may further comprise at least one cosmetically or dermatologically acceptable additive such as a thickener, a film former, a plasticizer, an antioxidant, an essential oil, a preserving agent, a fragrance, a filler, a pasty fatty substance, a waxy fatty substance, a neutralizing agent, and a polymer, and cosmetically active agents and/or dermatological active agents such as, for example, emollients, moisturizers, vitamins, essential fatty acids and medicaments.

Fillers that may be used in the compositions of the invention include, for example, silica powder; talc; polyamide particles and especially those sold under the name Orgasol by the company Atochem; polyethylene powders; microspheres based on acrylic copolymers, such as those based on ethylene glycol dimethacrylate/lauryl methacrylate copolymer sold by the company Dow Corning under the name Polytrap; expanded powders such as hollow microspheres and especially the microspheres sold under the name Expancel by the company Kemanord Plast or under the name Micropearl F 80 ED by the company Matsumoto; powders of natural organic materials such as crosslinked or noncrosslinked corn starch, wheat starch or rice starch, such as the powders of starch crosslinked with octenyl succinate anhydride, sold under the name Dry-Flo by the company National Starch; silicone resin microbeads such as those sold under the name Tospearl by the company Toshiba Silicone; clays (bentone, laponite, saponite, etc.); and mixtures thereof.

The fillers may be present in the composition of the invention in an amount ranging from about 0.1% to about 50% by weight, such as from 0.5% to about 30% by weight, and such as from about 1% to about 20% by weight, all weights based on the weight of the composition as a whole.

It has been surprisingly discovered that the composition of the present invention is transfer resistant and long wearing, and at the same time, provides superior comfort, feel and cushioning.

It has also been surprisingly discovered that the association of a polypropylsilsesquioxane wax substituted with alkyl units having at least 30 carbons, a siloxysilicate resin, and a polyorganosiloxane-containing polymer in the presence of a volatile solvent results in the formation of an anhydrous composition having long wearing, transfer resistant properties on skin, such as the lips and the face, while providing superior comfort, feel and cushioning. Moreover, the addition of a non-volatile solvent to the composition can result in a composition that imparts shine or improved shine.

The present invention will be better understood from the examples which follow, all of which are intended for illustrative purposes only.

EXAMPLES

A lip composition in accordance with the present invention was formulated. The ingredients employed are found in Table 1, below.

Procedures:
Procedure:
Phase A: 17% of Isododecane was weighed out and added to a beaker. Then 17% of MQ® resin was weighed out and added to the beaker and the two were mixed using a propeller at about 350 rpm until the MQ® resin was completely dissolved in the isododecane. Next 1.5% of lauroyl lysine and the pigments were weighed out and added to the beaker and mixed until the Lauroyl Lysine was dissolved and the pigments were wet. Next 25% of Bentone Gel was weighed out and added to the beaker and mixed until a smooth creamy texture was observed. The above mixture was then transferred to the disconti mill and ground until the pigments were completely dispersed.

Phase B:
In a separate beaker, 17.33% of isododecane, 11.33% of PSPA and 0.50% of silicone resin wax were weighed out and added to the beaker and allowed to heat at around 90 C until the PSPA and the Silicone resin wax were fully dispersed. The temperature source was then turned off and the batch was allowed to cool. The above Phase A was then added to phase B and the mixing was continued. When the batch reached around 65 C, pearls and fragrance were then added. The batch was then dropped at around 60 C. The batch was weighed to check for weight loss. Any weight loss was offset by adding isododecane.

The complete process was closely monitored and performed under closed kettle conditions to reduce the loss of isododecane.

| TRADE NAME/US-EU INCI NAME/ COMMERCIAL NAME | Comparative example | Inventive example |
|---|---|---|
| MQ ® RESIN/TRIMETHYLSILOXYSILICATE/ SR 1000 | 17 | 17 |
| PSPA/NYLON-611/DIMETHICONE COPOLYMER/DOW CORNING 2-8179 ® GELLANT | 11.33 | 11.33 |
| T-PROPYL RESIN WAX/C30-45 ALKYLDIMETHYLSILYL POLYPROPYLSILSESQUIOXANE (and) PARAFFIN/DOW CORNING ® SW-8005 C30 RESIN WAX | 0 | 1 |
| BENTONE GEL/DISTEARDIMONIUM HECTORITE (and) PROPYLENE CARBONATE/ BENTONE GEL ISD V | 25 | 25 |
| LAUROYL LYSINE/AMIHOPE LL | 1.5 | 1.5 |
| ISODODECANE/ISODODECANE | 37.57 | 36.57 |
| IRON OXIDES (CI 77499)/SICOVIT NOIR 85 E 172 | 0.626 | 0.626 |
| YELLOW 6 LAKE (CI 15985) SUNCROMA FD&C YELLOW 6 AL LAKE C70-5270 | 1.447 | 1.447 |
| RED 7 (CI 15850)/UNIPURE RED LC 3079 OR | 1.242 | 1.242 |
| RED 28 LAKE (CI 45410)/SUNCROMA D&C RED 28 AL LAKE C14-6623 | 0.35 | 0.35 |
| MICA (CI: 77019) | 3.834 | 3.834 |
| FRAGRANCE/PARFUM/ | 0.1 | 0.1 |
| EXTREME WEAR SCORE (after meal) | 66.8 +/− 17.9 | 88.2 +/− 4.8 |
| TRANSFER SCORE (after 5 minutes of application) | 1.3 +/− 0.5 | 1.0 +/− 0 |

One of ordinary skill in the art would expect the addition of a silicone wax to the above formulation would result in a decrease in wear/transfer resistance, as waxes are known in the industry to negatively impact these properties. The inventors have surprisingly and unexpectedly discovered, however, that the wax has instead improved the wear/transfer resistance properties as demonstrated by the higher wear score and the lower transfer score in the table above, while at the same time, increasing the comfort level on the wearer's lips.

What is claimed is:
1. A composition comprising:
(a) from 0.5 to about 2.5% by weight, based on a weight of the composition, of C30-45 alkyldimethylsilyl polypropylsilsesquioxane wax;
(b) about 5 to about 30% by weight, based on the weight of the composition of trimethylsiloxysilicate;
(c) from about 5 to about 25% by weight, based on the weight of the composition of nylon-611/dimethicone copolymer;

(d) from about 25 to about 70% by weight, based on the weight of the composition of at least one volatile solvent;

(e) optionally, at least one non-volatile solvent; and (f) at least one colorant, wherein said composition is anhydrous.

2. The composition of claim 1 wherein (b) is present in the composition in an amount of from about 15 to about 20% by weight, based on the weight of the composition.

3. The composition of claim 1 wherein (c) is present in the composition in an amount of from about 10 to about 15% by weight, based on the weight of the composition.

4. The composition of claim 1 wherein (e) is present in the composition in an amount of from about 1 to about 40% by weight, based on the weight of the composition.

5. The composition of claim 1, wherein (b) is present in the composition in an amount of from about 15 to about 20% by weight, based on the weight of the composition; (c) is present in the composition in an amount of from about 10 to about 15% by weight, based on the weight of the composition; and (e) is present in the composition in an amount of from about 1 to about 40% by weight, based on the weight of the composition.

6. The composition of claim 1, wherein a volatile solvent is isododecane.

7. The composition of claim 1, which is in the form of a lip stick adapted to apply the composition to the lips.

8. The composition of claim 1, which is a cream.

9. The composition of claim 1, wherein the composition does not comprise any wax other than the C30-45 alkyldimethylsilyl polypropylsilsesquioxane wax.

10. A method of making up a keratinous substrate comprising applying onto the keratinous substrate the anhydrous composition of claim 1.

11. A composition consisting of:

(a) from 0.5 to about 2.5% by weight, based on the weight of the composition of C30-45 alkyldimethylsilyl polypropylsilsesquioxane wax;

(b) about 5 to about 30% by weight, based on the weight of the composition of trimethylsiloxysilicate;

(c) from about 5 to about 25% by weight, based on the weight of the composition of nylon-611/dimethicone copolymer;

(d) from about 25 to about 70% by weight, based on the weight of the composition of at least one volatile solvent;

(e) optionally, at least one non-volatile solvent; and (f) at least one colorant, wherein said composition is anhydrous.

12. The composition of claim 11, wherein (b) is present in the composition in an amount of from about 15 to about 20% by weight, based on the weight of the composition; (c) is present in the composition in an amount of from about 10 to about 15% by weight, based on the weight of the composition; and (e) is present in the composition in an amount of from about 1 to about 40% by weight, based on the weight of the composition.

13. The composition of claim 11, wherein a volatile solvent is isododecane.

14. The composition of claim 11, which is in the form of a lip stick adapted to apply the composition to the lips.

15. The composition of claim 11, which is a cream.

* * * * *